United States Patent [19]

Miwa et al.

[11] Patent Number: 4,678,799
[45] Date of Patent: Jul. 7, 1987

[54] 1,2(1,4)-DIMETHYL-4(2)-(2-HYDROXYETHYL)-5-NITRO-IMIDAZOLE ANTIPROTOZOAL AGENTS WITH REDUCED MUTAGENICITY

[75] Inventors: Gerald T. Miwa, Maplewood; John S. Walsh, Avenel, both of N.J.

[73] Assignee: Merck & Co., Inc., Rahway, N.J.

[21] Appl. No.: 685,944

[22] Filed: Dec. 24, 1984

[51] Int. Cl.⁴ .................. A61K 31/415; C07D 233/94
[52] U.S. Cl. ..................................... 514/398; 548/339
[58] Field of Search ........................ 548/339; 514/398

[56] References Cited

U.S. PATENT DOCUMENTS 3,646,027  2/1972  Carlson et al. ....................... 514/398

OTHER PUBLICATIONS

Maron et al., 113 Mutation Research, pp. 173–215, (1983).
Brady et al., 42 Cancer Research, pp. 2592–2597, (1982).
Miwa et al., Biological Reactive Intermediates III, Kacsis (Edit.), pp. 527–535 (1986).
Goldman, The Johns Hopkins Medical J., 147, pp. 1–9, (1980).
Robbie et al., J. Obstet. Gynecol., 145, pp. 865–881 (1983).
Miwa et al., Chem. Biol. Interactions, 50, pp. 189–202 (1984).
McCann et al., Proc. Nat. Acad. Sci. USA, 72, 5135–5139 (1975).

Primary Examiner—Henry R. Jiles
Assistant Examiner—Kurt G. Briscoe
Attorney, Agent, or Firm—David L. Rose; Michael C. Sudol, Jr.

[57] ABSTRACT

A group of 4-substituted-5-nitroimidazoles is described, having effective antiprotozoal activity with much less mutagenicity than is shown by known 5-nitroimidazoles.

5 Claims, No Drawings

1,2(1,4)-DIMETHYL-4(2)-(2-HYDROXYETHYL)-5-NITRO-IMIDAZOLE ANTIPROTOZOAL AGENTS WITH REDUCED MUTAGENICITY

STATEMENT OF THE INVENTION

This invention relates to a new class of 4-substituted-5-nitroimidazoles having effective antiprotozoal activity and greatly reduced mutagenicity problems. More specifically, it relates to the compounds:
2-(1,4-dimethyl-5-nitroimidazole)-methylcarbamate;
1,4-dimethyl-2-(2-hydroxyethyl)-5-nitroimidazole;
1,2-dimethyl-4-(2-hydroxyethyl)-5-nitroimidazole
including esters thereof, particularly the pivaloyl ester.

BACKGROUND OF THE INVENTION

The compound 1-methyl-5-nitroimidazole-2-yl methylcarbamate, known as ronidazole, has long been known (U.S. Pat. No. 3,646,027) to be a potent agent to decrease the activity of protozoa and bacteria. It, however, suffers from severe handicaps to any practical use for this purpose because of high drug residual levels and strong mutagenicity, which render it impractical for animals to be used for human consumption. There is, thus, a strong need for a drug of like potency which would not have these deleterious side effects.

DESCRIPTION OF THE INVENTION

We have found that certain 1,2,4-substituted-5-nitroimidazoles are potent antiprotozoal and/or antibacterial agents with little or no mutagenic and drug residue level problems. The compounds are 2-(1,4-dimethyl-5-nitroimidazole)-methylcarbamate; 1,4-dimethyl-2-(2-hydroxyethyl)-5-nitroimidazole; and 1,2-dimethyl-4-(2-hydroxyethyl)-5-nitroimidazole, and esters, particularly the pivaloyl ester, thereof.

ADVANTAGES OF THE INVENTION

The demonstration in vitro (see Table I) that 4-substitution reduces DNA damage from 100% to less than 6% clearly demonstrates the prime advantage of these compounds, namely that the mutagenicity which condemns ronidazole type compounds can be and has been eliminated, so as to produce usable agents.

PREPARATION OF THE INVENTION

The compounds of this invention are prepared from 4-methylimidazole and its derivatives by known methods. Thus, to prepare (1,4-dimethyl-5-nitroimidazole-2-yl)methylcarbamate, 4-methylimidazole is nitrated in the 5-position and then methylated in the 1-position. The resultant 1,4-dimethyl-5-nitroimidazole is reacted with formaldehyde to introduce a hydroxy methyl group in the 2-position and the latter is reacted with methyl carbamate to give the compound.

1,4-Dimethyl-2-(2-hydroxyethyl)-5-nitroimidazole and 1,2-dimethyl-2-(2-hydroxyethyl)-5-nitroimidazole are prepared from 1,2,4-trimethyl-5-nitroimidazole by reaction with paraformaldehyde under pressure. By varying the reaction conditions one or the other compound, or mixtures thereof can be prepared.

The nitration and methylation reactions are carried out using well-known techniques such as nitration with concentrated nitric and sulfuric acids, and methylation with dimethyl sulfate.

The reaction to prepare the hydroxymethyl intermediate and the hydroxyethyl compounds are carried out using aqueous formaldehyde or paraformaldehyde under pressure at an elevated temperature. The reaction will add a hydroxymethyl group at the 2-position of a 2-unsubstituted compound or on one of the methyl groups on a methylated intermediate. The reaction condition for hydroxymethylation at a ring position are somewhat milder than for hydroxymethylation of a methyl group. Generally, the reaction is carried out in a solvent at from about 110° to 150° C., preferably about 125° C. for ring substitution and about 140° C. for methyl group substitution. The reaction is generally complete in about 20–30 hours, although prolonged reaction at high temperatures can result in the decomposition of some of the product. Because the reaction temperature is higher than the boiling point of the reaction mixture, the reaction is carried out in a sealed vessel such as a sealed tube or a glass lined bomb.

The solvent for the reaction can be water (formalin), dimethylsulfoxide (DMSO), acetonitrile, dioxane, and the like. Where the trimethyl compound is being hydroxymethylated, the choice of solvent can assist in directing the reaction to particular products. Where DMSO is used generally a mixture of 2- and 4-hydroxyethyl compounds is prepared which can be easily separated. However, it has been found that the use of acetonitrile or dioxane will produce predominantly the 2-substituted compound and water will predominantly produce the 4-compound. The products are isolated using techniques known to those skilled in the art.

The carbamates are prepared using sodium cyanate and trifluoroacetic acid in a solvent. The reaction is carried out in halogenated hydrocarbon such as methylene chloride, ethylene chloride, chloroform, and the like. The reaction mixture is generally at about 10°–30° C., preferably room temperature for about 2½ to 3½ hours. The reaction products are isolated using known techniques.

The esters of the instant compounds at the unreacted hydroxy groups are prepared using known esterification techniques. The preferred ester is the pivaloyl ester.

Enterohepatitis is a disease occurring primarily in turkeys and is caused by the protozoan parasite *Histomonas meleagridis*. It is also known as turkey blackhead disease. The 1,2,4-trisubstituted-5-nitroimidazoles of this invention are useful in the prevention and treatment of this disease and for this purpose are administered to turkeys mixed with an element of turkey sustenance, i.e., in the feed or drinking water. Although the optimum dose level will depend on the particular compound employed and the severity of the infection, good control of enterohepatitis is obtained by orally administering to the turkeys a feed containing from about 0.03% to about 0.1% by weight of the nitroimidazole. When the material is administered via the drinking water, somewhat higher levels may be employed, especially for therapeutic use. For instance, the drinking water may contain up to about 0.2% by weight of the active ingredient with good results. Those substances previously mentioned as preferred anti-trichomonal agents are also among those preferred in combating turkey blackhead.

As previously stated, the 1,2,4-trisubstituted-5-nitroimidazoles described herein may also be employed against trypanosomiasis and amoebiasis. In addition, certain of them, particularly 1,2-dimethyl-5-nitroimidazol-2-yl-methylcarbamate, possesses activity against the pleuro-pneumonia like organisms which have come to be known as PPLO organisms.

The imidazolylalkyl carbamates are effective against PPLO organisms when the compound is administered to fowl or swine in feed containing from about 0.003% to about 0.1% by weight of carbamate. The preferred dosage level, however, is between from about 0.003% to 0.08% by weight.

The 1,2,4-substituted-5-nitroimidazoles of this invention have antiprotozoal activity, and are particularly active against the causative organisms of the protozoal parasitic diseases trichomoniasis and enterohepatitis. Certain of them are also effective against amoebiasis and trypanosomiasis, as well as against the PPLO organisms and schistosomes. It will, of course, be understood that the compounds differ in their degree of efficacy against these various organisms.

Trichomoniasis is a protozoan disease caused by parasites of the genus *Trichomonas.* The compounds of the invention are effective against the particularly troublesome form of trichomoniasis known as *T. vaginalis vaginitis,* caused by infestation of the vagina with *T. vaginalis.* In treating this disease, the imidazolylalkyl carbamates may be administered either orally or topically. For oral administration unit dosage, forms such as tablets or capsules are normally employed which may contain from about 50 to about 500 mg of active ingredient. These are prepared by techniques known in the art, and contain the usual diluents, granulating agents, extenders and/or lubricating agents known to be satisfactory for the compounding of tablets and capsules. It is preferred to administer the compounds of the invention orally at a dose level of from about 25–1,000 mg/day, in either single or divided doses with divided doses being used more frequently than a single daily dose. An example of a suitable compressed tablet is the following:

| Component | Mg. per tablet |
| --- | --- |
| 2-(1,4-dimethyl-5-nitroimidazole)-methylcarbamate | 250 |
| Dicalcium phosphate | 100 |
| Lactose | 75 |
| Starch | 50 |
| Guar gum | 12 |
| Magnesium stearate | 2–3 |

If desired, tablets may be sugar coated or enteric coated by standard techniques. Alternatively, the antitrichomonal agent may be formulated in capsule form using fillers such as lactose, starch or kaolin. A typical capsule would contain 250 mg of, for instance, 2-(1,4-dimethyl-5-nitroimidazol)methylcarbamate, 2–3 g of magnesium stearate and about 75 mg of lactose in a No. 0 size capsule. Tablets and capsules containing smaller quantities of active ingredient may be made by reducing proportionately the amounts of excipients and diluents illustrated above. Alternatively, the compounds may be administered orally in liquid pharmaceutical vehicles such as solutions, emulsions, syrups or suspensions containing the diluents, flavoring agents and preservatives customarily employed in the pharmaceutical art.

For topical application, vaginal creams or suppositories containing the active ingredient may be used. To illustrate, a cream is prepared by mixing sufficient quantities of hydrophilic ointment and water, containing from about 5–10% by weight of compound, in sufficient quantities to produce a cream having the desired consistency.

This invention can be further illustrated by the following examples.

EXAMPLE 1

1,2,4-Trimethyl-5-nitroimidazole

A. Sulfuric acid (30 ml, 0.56 mole) was added dropwise to 2,4-dimethylimidazole (10 g, 0.104 mole), and urea (6.24 g, 0.104 mole), in a 1 l. flask cooled in ice. This was followed by the addition of fuming nitric acid (30 ml, 0.72 mole). When all had been added, the flask was heated at 200° C. for 1–2 minutes, whereupon a vigorous reaction ensued, necessitating the removal of the heat. When the reaction subsided, heating is continued for 10 minutes. The flask was then allowed to cool, and the reaction mixture was added to 300 ml of $H_2O$. The solution was adjusted to pH 5 with aqueous sodium hydroxide (about 40 g of sodium hydroxide was required). The resulting precipitate was filtered off and dried in vacuum to give 9.9 g of 2,4-dimethyl-5-nitroimidazole.

B. 2,4-dimethyl-5-nitroimidazole (7.0 g, 0.05 mole) and dimethylsulfate (7.0 ml, 0.074 mole) were heated at 100° C. for 1 hour 50 minutes. After cooling to room temperature, the reaction mixture was added to about 60 ml of water. Solid sodium bicarbonate was added until the solution is basic, and the mixture was then cooled on ice. The resulting crystals were filtered off and dried to give 6.2 g. This was recrystallized from water to give 4.5 g of 1,2,4-trimethyl-5-nitroimidazole.

EXAMPLE 2

1,4-Dimethyl-2-(2-hydroxyethyl)-5-nitroimidazole

Paraformaldehyde (4.05 g, 0.135 mole) and 5-nitro-1,2,4-trimethylimidazole (4.2 g, 0.027 mole) were combined in 25 ml of DMSO and heated at 140° C. for 48 hours (24 hours are found to be optimum), in a 300 ml glass-lined bomb. The reaction mixture was then evaporated in vacuo at 80° C. to give a dark brown oil. This was dissolved in about 60 ml of water, 5 ml of concentrated ammonium hydroxide are added, and the mixture was extracted six times with 70 ml of ethyl acetate. The ethyl acetate layers were dried over sodium sulfate and evaporated to give 3.74 g of residue. The crude product was dissolved in 3% methanol/chloroform to give a final volume of 8 ml. This is chromatographed preparatively on a partisil M20/50 column, eluting with 3% methanol/chloroform at 10 ml/min., with 4×2 ml injections. The product eluting at 46–55 minutes was collected. Combining the cuts from the four injections and evaporation of solvent gave 600 mg. This major product was a yellow oil which crystallized only with difficulty. The material was rechromatographed preparatively on a Whatman ODS-3 column eluting with 25% Methanol/water at 10 ml/min. The major peak was collected, and the solvent was evaporated to give 390 mg of pale yellow oil which readily crystallized on cooling. This product was 1,4-dimethyl-2-(2-hydroxyethyl)-5-nitroimidazole.

EXAMPLE 3

(1,4-Dimethyl-5-nitroimidazol-2-yl)methylcarbamate

A. 4-Methylimidazole (10 g, 0.12 moles), was cooled in a flask, and fuming nitric acid (11 ml, 0.24 moles) was added dropwise. This was followed by the addition of sulfuric acid (11 ml). The reaction was then heated with stirring at 100° C. for 2½ hours. The cooled reaction mixture was then added to 500 ml of ice water, and the precipitate was filtered off. The filtrate was neutralized with ammonium hydroxide, and filtered again. The combined precipitates were then recrystallized from water to give 6.35 g of 4-methyl-5-nitroimidazole.

B. 4-Methyl-5-nitroimidazole (2 g, 0.0157 mole) and dimethylsulfate (1.9 ml, 0.020 mole) were heated in 14 ml of benzene for 3½ hours. The cooled reaction mixture was filtered and the solids were washed with acetone and recrystallized from ethanol to give 2.4 g of white crystals. This was dissolved in water (50 ml) made basic with 1N sodium hydroxide, and extracted with 3×50 ml of chloroform. After drying over sodium sulfate, the chloroform was evaporated to give 1.3 g of crystalline residue (1,4-dimethyl-5-nitroimidazole).

C. The 1,4-dimethyl-5-nitroimidazole (1.3 g, 0.01 mole) and paraformaldehyde (1.24 g, 0.041 mole) were heated in 10 ml of dimethylsulfoxide in a sealed tube at 125° C. for 67 hours. The reaction mixture was evaporated to dryness and the residual oil was dissolved in 50 ml of water. This was made basic with ammonium hydroxide, and extracted with 5×40 ml of ethyl acetate. Drying over sodium sulfate and evaporation gave 1.8 g of residue (powder). This was recrystallized from tetrahydrofuran/hexane to give 1.2 g, m.p. 113°–114.5° C. of 1,4-dimethyl-2-hydroxymethyl-5-nitroimidazole.

D. 1,4-Dimethyl-2-hydroxymethyl-5-nitroimidazole (1.2 g, 0.07 mole), methylcarbamate (7.5 g, 0.09 mole) and dibutyl tin oxide (50 mg, 0.26 mmole) are combined and heated under nitrogen at 150° C. for 5.5 hours. The reaction is diluted with 50 ml of water and stirred overnight at 4° C.

The resulting precipitate is filtered off and dried to give 0.9 g. HPLC analysis indicates 95% carbamate.

The aqueous filtrate is extracted with 3×30 ml of ethyl acetate and the ethyl acetate layers are evaporated to dryness. The residual oil is dissolved in 15 ml of 1N hydrochloric acid, and extracted four times with 20 ml of ether. The aqueous phase is made basic with concentrated ammonium hydroxide and extracted three times with 15 ml of ethyl acetate. Drying (sodium sulfate) and evaporation gives a residual oil, still containing methyl carbamate. This is slurried with 15 ml of ether for 1 hour. A yellow precipitate forms and is filtered, washed with ether and dried to give 200 mg. This is combined with the precipitate (0.9 g), and recrystallized from isopropanol to give 830 mg of (1,4-dimethyl-5-nitroimidazol-2-yl)methylcarbamate.

A sample is prepared for elemental analysis by dissolving in methanol, treatment with Norit A and filtration (Celite). After removal of solvent the residue is recrystallized from water.

Calc. for $C_7H_{10}N_4O_4$: C, 39.25; N, 4.67; N, 26.17. Found: C, 38.90; H, 4.78; N, 25.79.

The remainder (720 mg) is dissolved in 40% methanol/ethyl acetate (14 ml) filtered and purified by HPLC. System: Whatman PXS M20/50, 1% methanol /ethylacetate, 10 ml/min., UV 270 nm, ret. time 45 minutes. Evaporation of the appropriate cuts gives 590 mg of the product.

EXAMPLE 4

1,2-Dimethyl-4-(2-(hydroxyethyl)-5-nitroimidazole 1,2,4-Trimethyl-5-nitroimidazole (5.0 g), aqueous formalin (23 ml, 37%) and water (10 ml) were combined and heated in a glass-lined bomb at 125° C. for 24 hours. The reaction mixture was then extracted with 5×75 ml of ethyl acetate. The ethyl acetate layers were combined, dried over sodium sulfate, and evaporated to give 7.1 g residue. The residue was chromatographed on a silica gel column and eluted with 4% methanol/ethyl acetate. Approximately 1.0 g of crude product was obtained which was crystallized from methylethyl ketone/hexane to give 784 mg of crystalline product.

EXAMPLE 5

In Vitro Antiprotozoal Activity of 5-Nitroimidazoles

Several 5-nitroimidazoles have been tested for in vitro antiprotozoal activity against *T. foetus, T. vaginalis*, and *G. lamblia*. Table I is condensed from these data and demonstrates the effect of a substituent at $C_4$ on antiprotozoal activity. Preliminary data with mammalian hepatocytes demonstrated a marked reduction in DNA single strand breaks induced by the instant 4-methyl substituents compared to their respective parent compounds, I and II. Moreover, comparative bacterial mutagenicity data demonstrated a uniform and dramatic reduction in mutagenicity for all the instant 5-nitroimidazoles. Consequently, when the data are expressed as the ratio of antiprotozoal activity/mutagenicity and normalized to the same ratio for the known compound I and II (Table I, Efficacy Index), it becomes obvious that the 4-substituent greatly improves the efficacy of the drug. Compound V demonstrates the greatest gain in efficacy of the compounds tested.

TABLE I

IN VITRO Antiprotozoal and Genotoxicity Activities of 5-Nitroimidazoles

| | | | | Activity $IC_{50}$ (μg/ml) | | | Efficacy Index[a] | | Extent of DNA Damage (%)[b] |
|---|---|---|---|---|---|---|---|---|---|
| | $R_1$ | $R_2$ | $R_3$ | T. Foetus | T. vaginalis | G. lamblia | T. foetus | T. vaginalis | |
| I (Ronidazole) | $CH_3$ | $CH_2OCNH_2$ (O=) | H | 0.42 | 0.54 | 0.9 | 1.0 | 1.0 | 100 |
| II (Flagyl) | $CH_2CH_2OH$ | $CH_3$ | H | 0.43 | 0.58 | 2.0 | 16.3 | 15.5 | 100 |
| III | $CH_3$ | $CH_2OCNH_2$ (O=) | $CH_3$ | 1.0 | 1.9 | 25 | 16.8 | 11.4 | 6 |
| IV | $CH_3$ | $CH_2CH_2OH$ | $CH_3$ | 1.9 | 12.5 | 25 | 24.6 | 4.8 | |

TABLE I-continued
IN VITRO Antiprotozoal and Genotoxicity Activities of 5-Nitroimidazoles

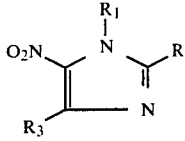

| | | | | Activity IC$_{50}$ (μg/ml) | | | Efficacy Index[a] | | Extent of DNA Damage (%)[b] |
|---|---|---|---|---|---|---|---|---|---|
| | R$_1$ | R$_2$ | R$_3$ | T. Foetus | T. vaginalis | G. lamblia | T. foetus | T. vaginalis | |
| V | CH$_3$ | CH$_3$ | CH$_2$CH$_2$OH | 5.25 | 9.0 | 25 | 80.0 | 60.0 | |

[a]Efficacy Index is defined as the ratio of antiprotozoal activity/mutagenicity for the test compound relative to this ratio for the known compound I.

$$\text{Efficacy Index} = \frac{(IC_{50} \times \text{mutagenicity}) \text{ of compound I}}{(IC_{50} \times \text{mutagenicity}) \text{ of test compound}}$$

where the mutagenicity is expressed as percent of that of compound I.

[b]Mammalian rat hepatocyte single strand DNA breaks expressed as % relative to parent compound not containing 4-substituent.

What is claimed is:

1. A compound selected from the group consisting of:
   (A) 1,4-dimethyl-2-(2-hydroxyethyl)-5-nitroimidazole; and
   (B) 1,2-dimethyl-4-(2-hydroxyethyl-5-nitroimidazole.
2. The compound of claim 1 which is 1,4-dimethyl-2-(2-hydroxyethyl)-5-nitroimidazole.
3. The compound of claim 1 which is 1,2-dimethyl-4-(2-hydroxyethyl)-5-nitroimidazole.
4. A composition useful for the treatment of parasitic infections in animals which comprises an inert ingredient and an effective amount of a compound of claim 1.
5. A method for the treatment of parasitic infections in animals which comprises administering to an animal with parasitic infections, an effective amount of a compound of claim 1.

* * * * *